(12) United States Patent
Raju

(10) Patent No.: US 9,955,942 B2
(45) Date of Patent: May 1, 2018

(54) ULTRASONIC METHOD AND APPARATUS FOR MEASURING OR DETECTING FLOW BEHAVIOR OF A NON-SINUSOIDAL PERIODICITY

(71) Applicant: KONINKLIJKE PHILIPS N.V., Eindhoven (NL)

(72) Inventor: Balasundar Raju, Chester, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 14/733,093

(22) Filed: Jun. 8, 2015

(65) Prior Publication Data

US 2015/0265240 A1    Sep. 24, 2015

Related U.S. Application Data

(62) Division of application No. 12/161,983, filed as application No. PCT/IB2007/050296 on Jan. 29, 2007, now abandoned.

(60) Provisional application No. 60/764,838, filed on Feb. 3, 2006.

(51) Int. Cl.
| | |
|---|---|
| A61B 8/06 | (2006.01) |
| A61N 1/39 | (2006.01) |
| A61B 5/00 | (2006.01) |
| A61B 5/021 | (2006.01) |
| A61B 5/0402 | (2006.01) |

(Continued)

(52) U.S. Cl.
CPC .............. *A61B 8/06* (2013.01); *A61B 5/7207* (2013.01); *A61B 8/488* (2013.01); *A61B 8/5269* (2013.01); *A61N 1/3925* (2013.01);

*A61B 5/021* (2013.01); *A61B 5/0402* (2013.01); *A61B 8/08* (2013.01); *A61B 8/543* (2013.01)

(58) Field of Classification Search
CPC ......... A61B 8/06; A61B 5/7207; A61B 8/488; A61B 8/5269; A61B 5/021; A61B 5/0402; A61B 8/08; A61B 8/543; A61N 1/3925
See application file for complete search history.

(56) References Cited

U.S. PATENT DOCUMENTS

| | | | | |
|---|---|---|---|---|
| 4,513,249 A | * | 4/1985 | Baghdady | H04K 3/228 327/113 |
| 5,719,951 A | * | 2/1998 | Shackleton | G06K 9/00221 375/E7.026 |

(Continued)

FOREIGN PATENT DOCUMENTS

| | | |
|---|---|---|
| DE | 20003455 U1 | 5/2000 |
| DE | 10008886 A1 | 9/2001 |

(Continued)

OTHER PUBLICATIONS

Gibbons et al., Real-time calculation of ultrasonic pulsatility index, Med. & Biol. Eng. & Comput., 1981, 19, 28 34.*

(Continued)

*Primary Examiner* — Bo J Peng

(57) ABSTRACT

A method and apparatus for automated detection of a general, non-sinusoidal type of periodicity in ultrasound Doppler signals from pulsatile blood flow is described. The method computes a measure of pulsatility from the power spectrum near the peaks of the fundamental and harmonic frequencies of the Doppler signal information.

9 Claims, 6 Drawing Sheets

(51) Int. Cl.
*A61B 8/08* (2006.01)
*A61B 8/00* (2006.01)

(56) References Cited

U.S. PATENT DOCUMENTS

| | | | |
|---|---|---|---|
| 5,741,980 A * | 4/1998 | Hill | G01B 5/28 |
| | | | 73/861.04 |
| 6,080,107 A * | 6/2000 | Poland | A61B 8/481 |
| | | | 600/458 |
| 6,097,331 A * | 8/2000 | Matsugatani | G01S 7/35 |
| | | | 342/109 |
| 6,176,832 B1 * | 1/2001 | Habu | A61B 5/0285 |
| | | | 600/485 |
| 6,179,781 B1 | 1/2001 | Phillips | |
| 6,185,457 B1 | 2/2001 | Kroll et al. | |
| 6,213,947 B1 | 4/2001 | Phillips | |
| 6,213,951 B1 | 4/2001 | Krishnan et al. | |
| 6,334,045 B1 | 12/2001 | Green et al. | |
| 6,398,733 B1 * | 6/2002 | Simopoulos | G01S 7/52026 |
| | | | 600/443 |
| 6,428,479 B1 * | 8/2002 | Aksnes | A61B 8/06 |
| | | | 600/458 |
| 6,440,082 B1 | 8/2002 | Joo et al. | |
| 6,560,484 B1 | 5/2003 | Kroll et al. | |
| 6,571,193 B1 * | 5/2003 | Unuma | A43B 3/0005 |
| | | | 340/853.2 |
| 6,626,836 B2 | 9/2003 | Mao et al. | |
| 6,632,177 B1 | 10/2003 | Phillips et al. | |
| 6,786,917 B1 | 9/2004 | Schiller et al. | |
| 6,898,452 B2 | 5/2005 | Al-Ali et al. | |
| 2001/0034485 A1 | 10/2001 | Kawagishi et al. | |
| 2001/0044278 A1 * | 11/2001 | Chiao | A61B 8/06 |
| | | | 455/67.11 |
| 2001/0056236 A1 * | 12/2001 | Angelsen | A61B 8/06 |
| | | | 600/458 |
| 2002/0004636 A1 | 1/2002 | Tsubata | |
| 2002/0173725 A1 | 11/2002 | Rock et al. | |
| 2005/0049503 A1 | 3/2005 | Schoisswohl et al. | |

FOREIGN PATENT DOCUMENTS

| | | | | |
|---|---|---|---|---|
| JP | 200574225 A | | 3/2005 | |
| JP | 2005177494 A | * | 7/2005 | A61B 8/06 |

OTHER PUBLICATIONS

Raju et al:"A Novel Ultrasound Based Automated Pulsatile Flow Detection Medthod for Resuscitation"; Proceedings of the IASTED International Conference on Biomedical Engineering, XX,SS, Feb. 16, 2005, pp. 325-330.

* cited by examiner

ULTRASONIC METHOD AND APPARATUS FOR MEASURING OR DETECTING FLOW BEHAVIOR OF A NON-SINUSOIDAL PERIODICITY

CROSS REFERENCE TO PRIOR APPLICATION

This application is a divisional application of U.S. patent application Ser. No. 12/161,983, filed on Jul. 24, 2008, which is the National Stage Application of PCT/IB2007/050296, filed Jan. 29, 2007, which claims the priority of U.S. Provisional Application No. 60/764,838, filed Feb. 3, 2006, the entire contents of which are incorporated herein by reference.

The present invention relates generally to the field of medical ultrasound diagnostics and, more specifically, to a method and apparatus for ultrasonically measuring and/or detecting flow of a non-sinusoidal periodicity.

Early defibrillation is critical for successful resuscitation of a sudden cardiac arrest patient. The absence of a detectable cardiac pulse in a patient is a strong indicator of cardiac arrest. Defibrillators currently do not assess the patient's heartbeat or blood circulation and the responder has to manually check for the pulse, a procedure known to be very subjective. Hence, an automated assessment of pulsatile blood flow would be important for an automated or manual defibrillator as well as in monitoring situations and other clinical applications. One example is continuous monitoring of a patient's vital signs in the intensive care unit (ICU), operating room, or the emergency room (ER). Another example is the assessment of the pulse of a cardiac arrest victim both before and after the application of a defibrillation shock. Defibrillation therapy is applied in cardiac arrest situations in order to convert non-perfusing electrical activity such as ventricular fibrillation to a normal rhythm. In these situations, it insufficient to monitor the patient's ECG alone, since the heart's electrical rhythm could appear normal, but be of a non-perfusing nature, such as in the case of pulseless electrical activity (PEA). It is important to determine whether the patient has regular and pulsatile blood circulation, the absence of which would indicate the need for cardiopulmonary resuscitation (CPR) and/or appropriate medications. Moreover such an assessment is preferably done in a continuous manner without user intervention, from the scene of a cardiac arrest event all the way to the ER and ICU.

Doppler ultrasound is a known tool for assessing blood flow and has been proposed for assessment of the state of the pulse of a cardiac victim. However the use of Doppler ultrasound for automated assessment without an image display and a trained person for interpretation is quite challenging. Making an assessment purely based on the total Doppler power is difficult since there is a need to select a suitable threshold. The total Doppler power measure is dependent on the strength of the backscattered echo, which depends on level of attenuation in the intervening tissues, as well as the scattering properties of the patient's blood. These parameters are highly variable from one patient to another, making a predetermined, fixed threshold impractical. In order to select a threshold, it is also necessary to have a precise characterization of the noise level in the electronics of the Doppler device. Relying on such a characterization is not a robust approach since a periodic self-characterization might be needed. Also unknown is the level of interference and motion artifacts that may contaminate the Doppler signal. Hence a simple threshold for deciding that flow exists may not be possible. Furthermore, the total Doppler power gives no indication of the regularity of the blood flow in that it does not determine whether the flow is pulsatile or not.

In order to address many of these issues, estimation of a periodicity index based on the Doppler power within a specific frequency band, e.g., 1-1.2 kHz, is described in the parent patent application. Hereafter, the Doppler power within a specific frequency band is referred to as the banded Doppler signal. When a sufficiently high enough Doppler frequency band is chosen, this signal when plotted as a function of time, fluctuates periodically from a high value during systole to a low value during diastole. The method of the parent application uses auto-correlations and Fourier transforms of the banded Doppler signal in order to determine whether there is periodicity in the banded Doppler signal. In this method, the fundamental peak frequency in the spectrum of the banded Doppler signal is first located. Then the ratio of the power within a narrow band around this fundamental frequency to the total power, termed pulsation index, is computed. This pulsation index is high when there is a periodic flow, and is low when a periodic flow is absent.

This technique is premised upon a model of pulsatile cardiac activity as sinusoidal. However cardiac blood flow pattern is not periodic in a purely sinusoidal manner since the time spent in systole is typically less than the time spent in diastole, and the shape is usually not a sinusoidal one. This usually leads to the presence of a few harmonics in the frequency spectrum. Hence a sinusoidal periodicity detection scheme may not be adequate in such cases, and the pulsation index would be lower than what it would be when the non-sinusoidal character of the periodicity is taken into account. Accordingly it is desirable that the measure or detection of pulsatile cardiac activity consider this non-sinusoidal character of the physiology.

In accordance with the principles of the present invention, an ultrasonic method and apparatus are described which take into account the non-sinusoidal behavior of pulsatile flow. This is done by the inclusion of several harmonic peaks in the computation of the pulsation index, while taking care to avoid peaks due to noise (when no flow exists). The noise level is computed by considering that, for pulsatile flow, the regions between the peaks in the spectrum must be due to noise. Comparison with a noise threshold derived from these regions ensures that valid pulsatile activity has been detected, aided by the frequency resolution in the spectrum being sufficiently high enough to individually resolve the fundamental and harmonic peaks of the flow spectrum, with the bandwidth being sufficiently small to ensure adequate separation of the main lobes of each of the peaks. This inventive method has the advantage that a better separation of the pulse and pulselessness states is possible. The calculated pulsation index would be much closer to unity for the pulse case and would still remain close to zero for the pulselessness case. This in turn leads to better sensitivity and specificity for pulse assessment.

In the drawings.

Herein, identical reference numerals are used, where possible, to designate identical elements that are common to the figures. The images in the drawings are conventionally simplified for illustrative purposes and are not depicted to scale.

The appended drawings illustrate examples of the invention and, as such, should not be considered limiting the scope of the invention that may admit to other equally effective embodiments.

Figure 1:
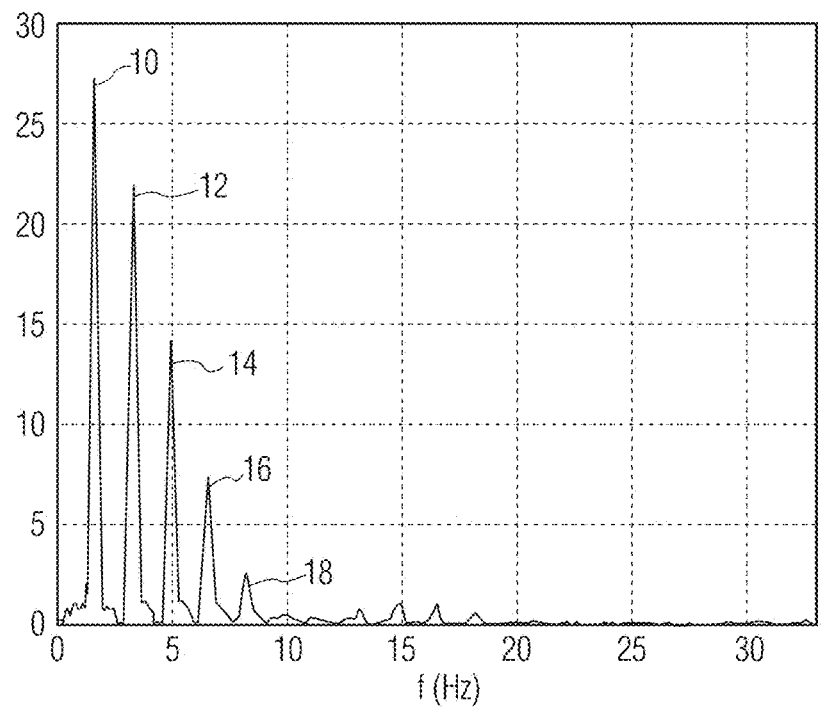
FIG. 1 illustrates a frequency spectrum of banded Doppler signals during normal, non-sinusoidal flow.

A pure sinusoidal function exhibits no harmonics and, when analyzed in the frequency domain, is seen to exhibit only a fundamental frequency component. However, the usual cardiac blood flow pattern is not a pure sinusoid. This is because the cardiac activity spends more time in diastole than systole, giving the flow pattern a non-sinusoidal character. When this characteristic is analyzed in the frequency domain it exhibits frequency peaks as illustrated in FIG. 1, which is a spectrum of a banded Doppler signal having a fundamental frequency component 10 at 1.64 Hz. The non-sinusoidal nature of the pulsatile activity gives the spectrum several harmonics of the fundamental. In this example higher harmonics 12, 14, 16, and 18 can be seen ranging up to about 8 Hz. In the following embodiment of the present invention the power within a small band around each fundamental and harmonic peak is compared to the total power in the banded Doppler signal in the assessment of pulsatility.

Figure 3:
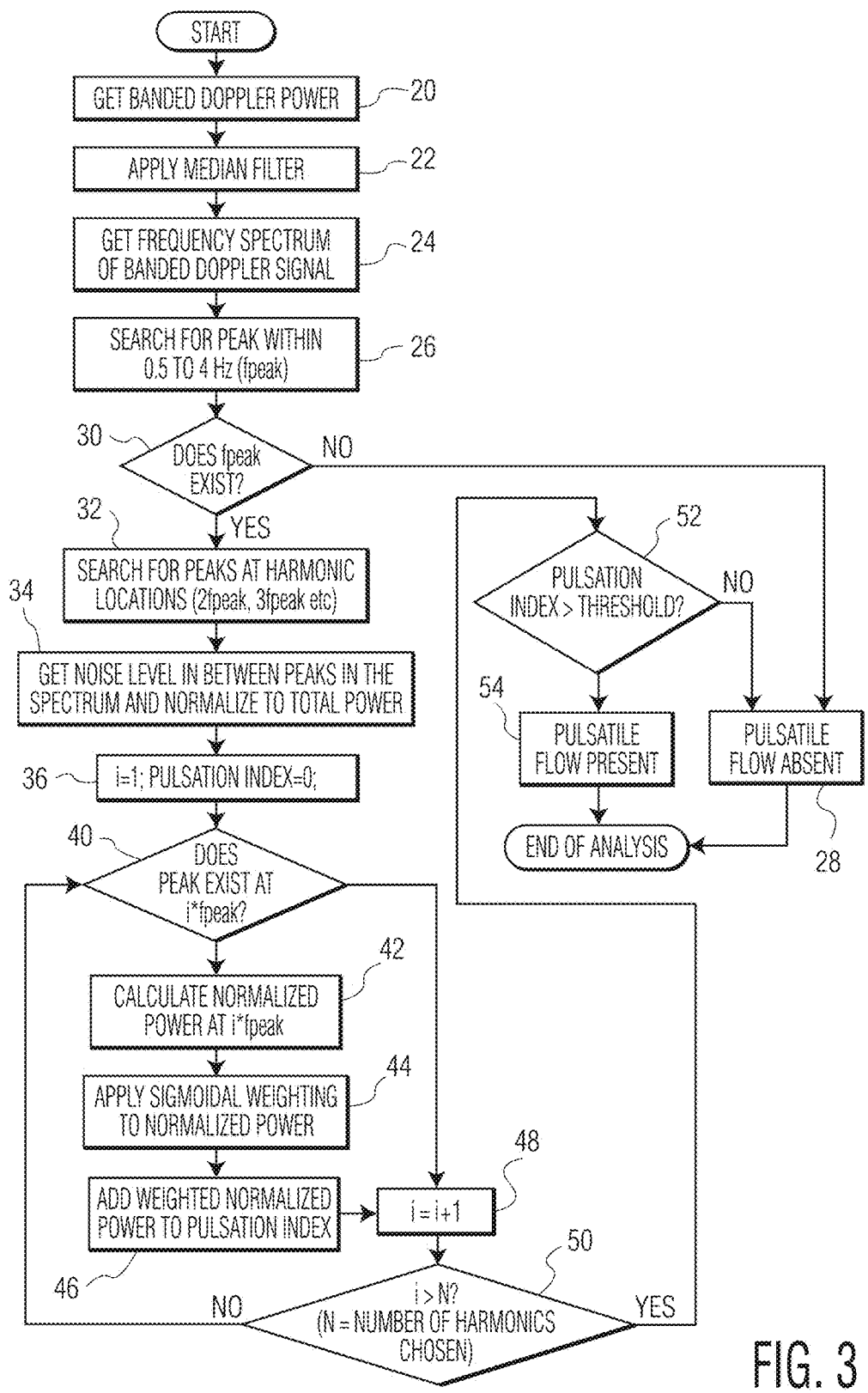
FIG. 3 illustrates a flowchart of a non-sinusoidal periodicity detection method of the present invention.

A flowchart illustrating a method of the present invention is shown in FIG. 3. As in the apparatus and method of the parent application, the banded Doppler signal within a certain frequency band, e.g., 1-1.2 kHz, is obtained in step 20. In step 22, a median filter is applied to the banded Doppler signal to improve assessment under noisy conditions, as supported by empirical studies. A non-linear filter like a median filter is desirable because of its ability to preserve the signal structure compared to a linear filter. The frequency spectrum of the filtered banded Doppler signal is obtained in step 24, which in this example is taken over a span of 5-second windows that are progressively marched in time in 1-second intervals. The calculation of the frequency spectrum can be done by taking the Fourier transform of the auto-correlation of the banded Doppler signal, or directly by any means commonly employed for power spectrum estimation (e.g., averaged periodogram, etc.) In step 26 the fundamental peak frequency (fpeak) in the spectrum is located through peak searching (using second derivative tests) within a frequency span that is physiologically meaningful such as 0.5 to 4 Hz. If no peak is located, then the method concludes at 28 with a determination of the absence of pulsatile flow and no further processing is done.

If a fundamental peak is found as a result of step 30, a peak-searching algorithm is conducted in step 32 in regions around the locations where harmonics are expected (2fpeak, 3fpeak, etc.) in order to determine if harmonics are present. Typically up to four harmonics may be searched, although a greater or lesser number of harmonic regions may be chosen in a particular implementation or for a particular patient signal. For each of the frequency peaks found (fundamental and harmonics, 10-18 in FIG. 1) in the spectrum, a normalized power ratio is computed in step 42 as the ratio of the power within a small bandwidth around the peak to the total power in the banded Doppler signal. Each peak is separately processed in the method of FIG. 3 by initializing the peak count to one and setting the pulsatile index to zero in step 36.

If pulsatile flow is present, then the normalized power ratios are expected to be high, with the highest value usually for the fundamental frequency 10, and progressively decreasing for each harmonic 12-18. If the sum total of these power ratios is taken to be the pulsation index, a normalized sum will have a value close to unity for the pulsatile flow case. However, when pulsatile flow is absent, then these power ratios (if peaks existed for the fundamental and harmonics) are simply based on noise. Summing these values would inadvertently raise the pulsation index leading to false positives in the pulse assessment.

To overcome this a noise level in the banded Doppler signal is determined at step 34. If periodic flow is present, then the spectrum can only have peaks at fundamental and harmonic locations, and regions in the spectrum between these peaks would constitute noise. Hence, once fundamental and harmonic locations 10-18 are determined, the method also looks at regions in between these peaks in step 34 and calculates a mean noise level. Alternatively, the noise level could be computed by looking at frequencies that are sufficiently high where no effects of pulsatile activity are expected.

Figure 2:
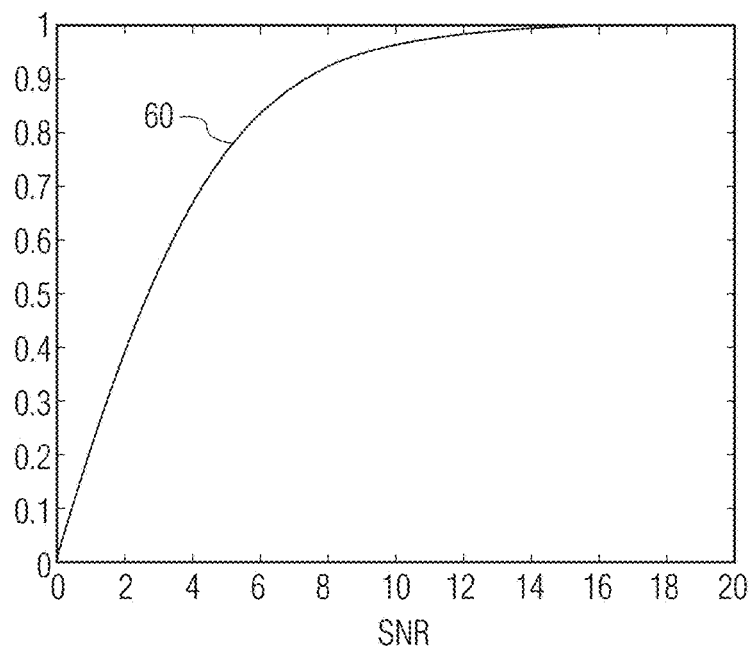
FIG. 2 illustrates a sigmoid weighting function used to suppress contributions from noise.

If each peak in the spectrum is truly significant (the flow case), then the SNR defined as the ratio of the power around the peak to the noise level, would be high. When flow does not exist, then the SNR would be low. Hence a suitable weighting function is applied in step 44 to the normalized power ratio contributed by each peak frequency (step 42) as illustrated by the sigmoid-type weighting function 60 shown in FIG. 2. The weighting function 60 suppresses contributions from the peaks if the SNR is low while still maintaining contributions from true peaks that have a high SNR. The sigmoid type function is of the form:

$$w = \frac{2}{1 + \exp(-ax)} - 1$$

where w is the weighting function, x is the SNR at a peak, and a is a shape parameter typically 0.4. Other weighting functions can be used as desired. Once the power ratio contribution due to a peak is weighted in step 44, the pulsation index is incremented by this weighted value in step 46. This is done for each of the peaks by incrementing the peak count in step 48, comparing the count to N, the number of harmonics used in the computation, in step 50, and repeating the computation for each peak. When all of the peaks have been included in the pulsation index the index is compared to a threshold in step 52. If the pulsation index is high enough there is pulsatile flow (54) and if not, then it is concluded that pulsatile flow is absent (28).

Figure 4A:
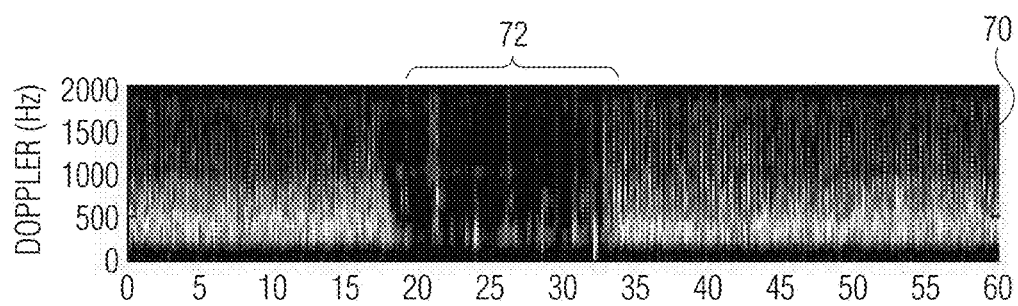
FIGS. 4a-4d illustrate a Doppler spectrogram and resulting pulsatility index, comparing a technique of the present invention with a technique of the parent application.
Figure 4B:
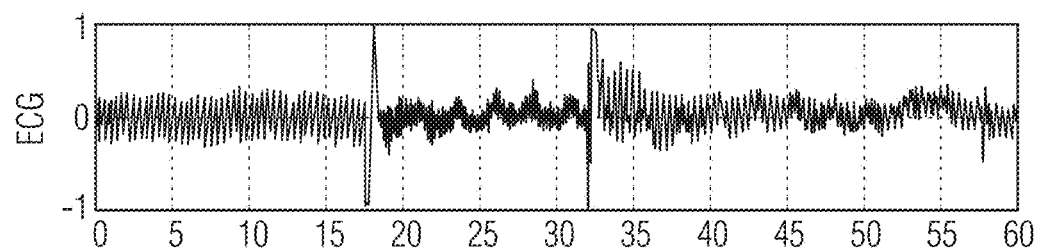
Figure 4C:
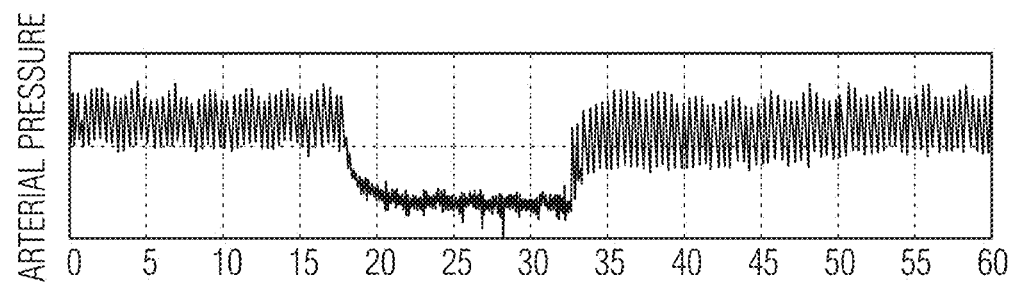
Figure 4D:
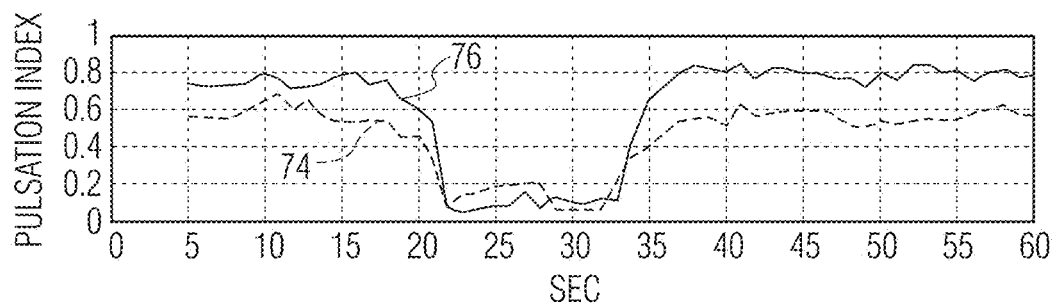

FIGS. 4a-4d compare the performance of an embodiment of the present invention with that of the technique of the parent application. FIG. 4a illustrates a Doppler spectrogram 70 of for a subject experiencing ventricular fibrillation during the interval 72. This event is also reflected in the ECG waveform of FIG. 4b and in the blood pressure graph of FIG. 4c. FIG. 4d shows a pulsation index 74 determined in accordance with the sinusoidal-based technique of the parent application, and a pulsation index 76 determined in accordance with a non-sinusoidal-based technique of the present invention. A comparison of the lines 74 and 76 show that the pulsation index 76 is higher during the pulsatile blood flow before and after the VF interval 72, and remains low during the non-pulsatile flow condition of interval 72.

Figure 5:
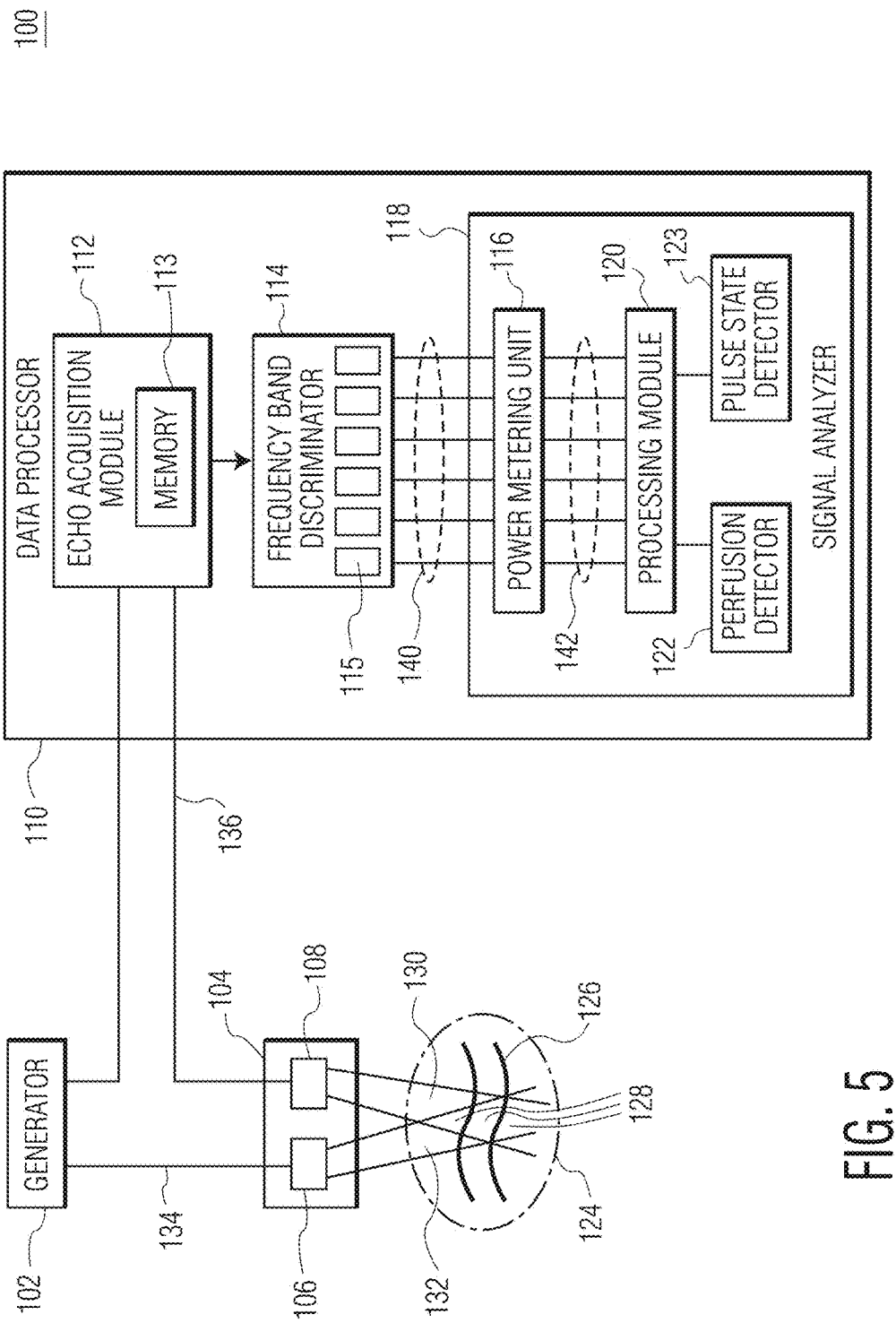
FIG. 5 depicts a block diagram of an exemplary apparatus of the kind that may be used for ultrasound diagnostics in accordance with one embodiment of the present invention.

FIG. 5 depicts a block diagram of an exemplary apparatus 100 of the kind that may be used for ultrasound diagnostics in accordance with one embodiment of the present invention. In one exemplary application, the apparatus 100 can perform assessment (e.g., detection and/or measurements) of perfusion and/or the pulse state of a patient. Herein the term "perfusion" refers to blood flow in a blood vessel (e.g., carotid artery) or a tissue. In other applications, the apparatus 100 may be used as a component in resuscitation systems and defibrillators, monitors and detectors of weak heart beat (e.g., fetal heart beat), among other medical diagnostic and clinical systems. Additionally, the apparatus 100 may also be used in non-medical systems for measuring, for example, flow or pulsatile activity of colloidal and emulsion solutions.

In one embodiment, the apparatus 100 comprises a generator 102, at least one ultrasonic transducer 104 (one transducer 104 is shown), and a data processor 110. In alternate embodiments, the transducers 104, together, form an array that typically is disposed upon an application pad (not shown), and the transducers may additionally be time multiplexed. Such arrays are disclosed, for example, in U.S. Pat. No. 6,565,914 to Rock et al.

In the depicted embodiment, the transducer 104 comprises a transmitter 106 and a receiver 108. In this embodiment, the generator 102 is generally a source of a continuous wave (CW) radio frequency (RF) signal (e.g., 1-10 MHz). In operation, the generator 102 via interface 134 activates (or excites) the transmitter 106 to emit ultrasound (illustratively shown as a beam 132) propagating in a portion 124 of the body of a patient located beneath the transducer. The receiver 108 collects, within an aperture 130, an acoustic echo signal (i.e., scattered ultrasound), transforms the echo signal into an electrical signal and transmits, via interface 136, to the data processor 110. The transmitter 106 and receiver 108 are positioned such that the beam 132 and aperture 130 overlap in a region 128 of a large blood vessel 126, such as a carotid artery, and the like.

In an alternate embodiment, the apparatus 100 may comprise the transducer 104 capable of operating as a transmitter when RF power is ON, or a receiver when the RF power is OFF, respectively. In this embodiment, the generator 102 produces pulsed RF power (PW) having duration of an ON time interval of about 0.2 to 20 microseconds and a duty cycle in a range of about 0.2 to 20%.

In one exemplary embodiment, the data processor 110 comprises a signal acquisition module 112, a frequency band discriminator 114, and a signal analyzer 118 including a processing module 120 which performs the non-sinusoidal pulsatility calculations described above, a perfusion detector 122, and a pulse state detector 123. Components of the data processor 110 may be reduced to practice in a form of electronic hardware, a computer program (i.e., software), or both. Alternatively, portions of signal processing performed by the module 110 may also be accomplished using a remote processor (not shown). Moreover, in another embodiment, the analysis may be performed in the analog, rather than the digital, domain, e.g., frequency band discriminator 114 could be replaced with an analog filter bank, data processor 110 could comprise a correlator, etc., as would be known to one of ordinary skill in the art.

The signal acquisition module 112 acquires the echo signal and defines a Doppler signal. Herein, the term "Doppler signal" relates to a signal that is proportional to a frequency shift between the incident ultrasound and the echo signal. Illustratively, the module 112 includes frequency converters of the echo signal, analog and digital filters, memory devices, computer processors, and other means conventionally used for data acquisition and digital signal processing. One filter may be a high frequency pass filter that suppresses the echo originated in the region 128 by stationary or slowly moving objects, such as tissues, walls of the blood vessel 126, the like. In one embodiment, the module 112 stores in a memory 113 in a digital format the Doppler signal that has been acquired during at least one time interval $\Delta T_1$ having duration of about 2 to 20 sec (preferably 5-10 sec). In this embodiment, from the memory 113, the stored digitized Doppler signal may be provided for further processing to the frequency band discriminator 114 in a form of consecutive data banks each relating to a time segment $\Delta T_2$ having duration of about 10 to 100 msec (e.g., 40 msec).

In one embodiment, the frequency band discriminator 114 comprises a plurality (e.g., 4 to 10) of band pass filters 115 (six filters 115 are shown), which selectively decompose the Doppler signal in a plurality of sampling signals 140. Each sampling signal 140 has a frequency range that represents a portion of a pre-selected frequency range of the Doppler signal, wherein such ranges do not overlap. Hereinafter, the terms "frequency range" and "frequency band" are used interchangeably. Together, frequency ranges of the sampling signals 140 comprise the frequency range of the decomposed Doppler signal or a portion of it.

The band pass filters are selectively calibrated to have the same coefficient of amplification that may be either greater or smaller than 1. As such, the sampling signals 140 preserve instant spectral power distribution of the Doppler signal as provided by the signal acquisition module 112 and, therefore, power of each sampling signal is proportional to the power of the Doppler signal in the frequency range of the respective sampling signal 140. In the depicted embodiment, an output of each band pass filter 115 is illustratively coupled to a respective input of the power metering unit 116. In an alternate embodiment (not shown), such outputs may be multiplexed (e.g., time multiplexed) and be coupled to the power metering unit 116 using a single transmission line.

The power metering unit 116 selectively calculates the power of each of the sampling signals 140 and outputs to the processing module 120 a plurality of signals 142 each representing the power of the respective sampling signal as averaged for duration of the time segment $\Delta T_2$. One skilled in the art will readily appreciate that the signals 142 may also be multiplexed (e.g., time multiplexed) and coupled to the processing module 120 using a single transmission line.

To assess the perfusion, in one exemplary embodiment the processing module 120 selectively computes a measure of periodicity of the Doppler signal selectively in each frequency band of the signal using, e.g., a ratio of the power of the Doppler signal to baseline noise. A peak value of the ratio and the data identifying the frequency band having such a ratio are transmitted to the perfusion detector 122. In the perfusion detector 122, the computed peak ratio is compared with pre-determined settings to assess a velocity of the blood flow in the examined blood vessel (e.g., carotid artery). Data relating to a specific pattern of the spectral power distribution of the Doppler signal may also carry additional diagnostic information regarding mechanical activity of the patient's heart and, as such, be preserved, e.g., in a memory of the signal analyzer 118 or, alternatively, data processor 110.

To assess a measure of periodicity of the Doppler signal and, as such, the state of the pulse, in one exemplary embodiment the processing module 120 selectively computes a measure of periodicity of the Doppler signal selectively in each fundamental and harmonic frequency band as described above. The aforementioned noise analysis is performed, and the contribution of each fundamental and harmonic signal is included in the pulsatility index. The pulsatility index so determined is validated against a threshold and presented to the user. One computational technique includes auto-correlation analysis of the power of the Doppler signal over a pre-determined time interval to determine if an auto-correlation function has periodically spaced peaks identifying a pulsatile activity of the heart. Results of the auto-correlation analysis are transmitted to the pulse state detector 123. In the pulse state detector 123, the intensity of blood pulsing may be assessed using, for example, a pulsation index as previously described and like measures of the periodicity. The computed value of the selected measure of periodicity may be compared with other pre-determined settings and/or thresholds to define and assess the state of the pulse in the blood vessel 126.

In one embodiment, the processing module 120 collects output signals 142 during a period of time that encompasses several cardiac cycles. Illustratively, the processing module 120 may acquire the signals 142, in a form of blocks of data each relating to the segment $\Delta T_2$, for duration of the time interval $\Delta T_1$ extending over several cardiac cycles and selectively process each such a block of data. The processing module 120 may utilize computational techniques known to those skilled in the art, such as algebraic and Boolean logic operations, spectral analysis, Fourier analysis (e.g., Fast Fourier transform (FFT) analysis), correlation analysis, and other signal processing techniques.

Figure 6:
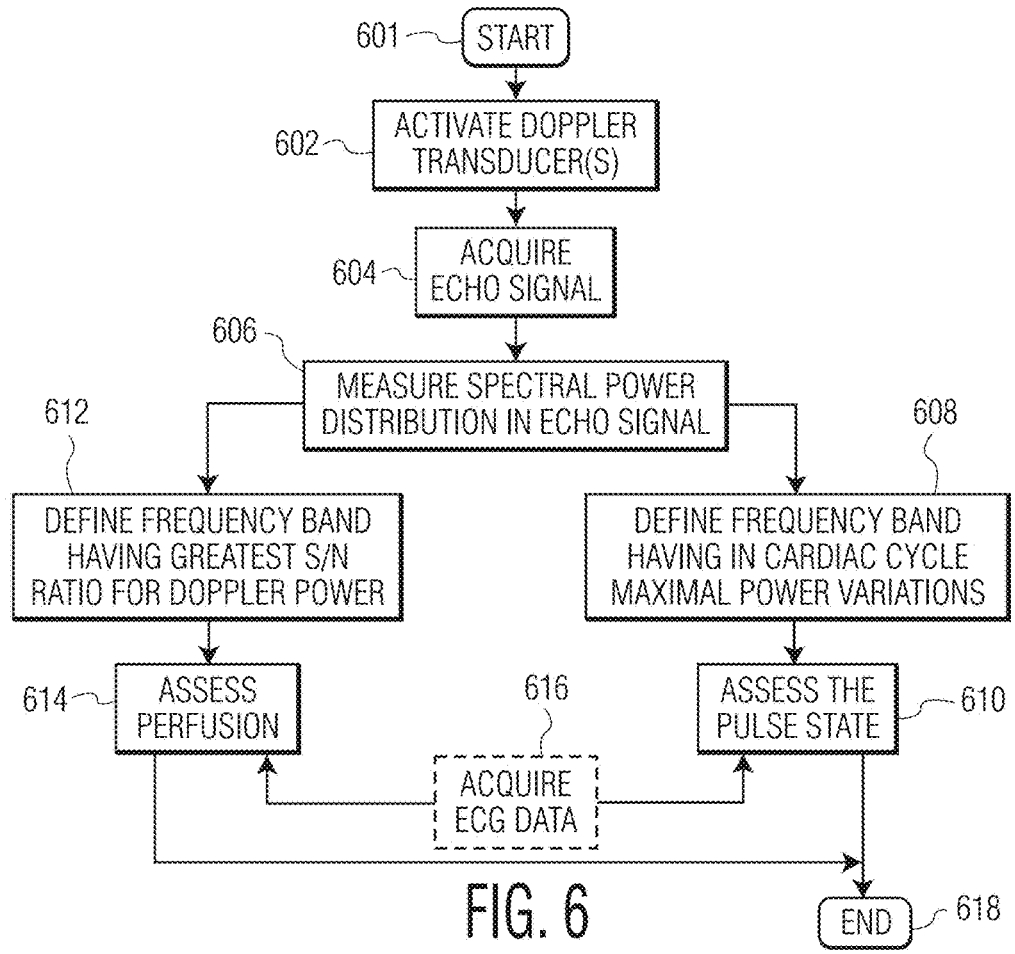
FIG. 6 depicts a flow diagram of one exemplary embodiment of the inventive method for ultrasound diagnostics that may be used during an illustrative procedure of assessing the perfusion or blood pulsing.

FIG. 6 depicts a flow diagram of one exemplary embodiment of the inventive method for ultrasound diagnostics. The method may be reduced to practice, e.g., using the apparatus of FIG. 5 for performing an illustrative procedure of detecting blood perfusion and/or the pulse state of a patient.

The method starts at step 601 and proceeds to step 602. At step 602, at least one ultrasonic transducer 104 is activated to emit ultrasound towards the blood vessel 126 (e.g., carotid artery) and collect the echo signal scattered in the region 128 of the body of a patient. The ultrasonic echo signal is converted to the electrical format and transmitted to the data processor 110. At step 604, the echo signal is acquired for duration of the time interval $\Delta T_1$, digitized, and stored in a memory, as discussed above in reference to FIG. 5. The time interval $\Delta T_1$ typically encompasses several (e.g., 3-6) cardiac cycles. Alternatively, the time interval $\Delta T_1$ may have a pre-determined duration. At step 606, spectral power distribution of the Doppler signal is defined in a plurality of discrete frequency bands and averaged within time segments $\Delta T_2$ of the time interval $\Delta T_1$. At step 608, a frequency band having, during a cardiac cycle, maximal periodic variations of the Doppler power is defined and, at step 610, the pulse state of the patient is calculated, as discussed in detail in reference to FIG. 3. At step 612, a frequency band having, during a cardiac cycle, a peak ratio of the Doppler power to baseline noise is defined and, at step 614, the perfusion is calculated as discussed above in reference to FIG. 5. At an optional step 616, data collected using simultaneously operating electrocardiograph (ECG system) may be used when, e.g., the method is reduced to practice in a defibrillating system, as discussed in reference to FIG. 7 below. In this case, timing of the ECG data should be conventionally adjusted for a time lag between the ECG and ultrasound spectrograms. In one embodiment, steps 608, 610, 612, 614, and 616 may be performed substantially simultaneously. Upon completion of steps 610 and 614, the method proceeds to step 618 where the method ends.

Figure 7:
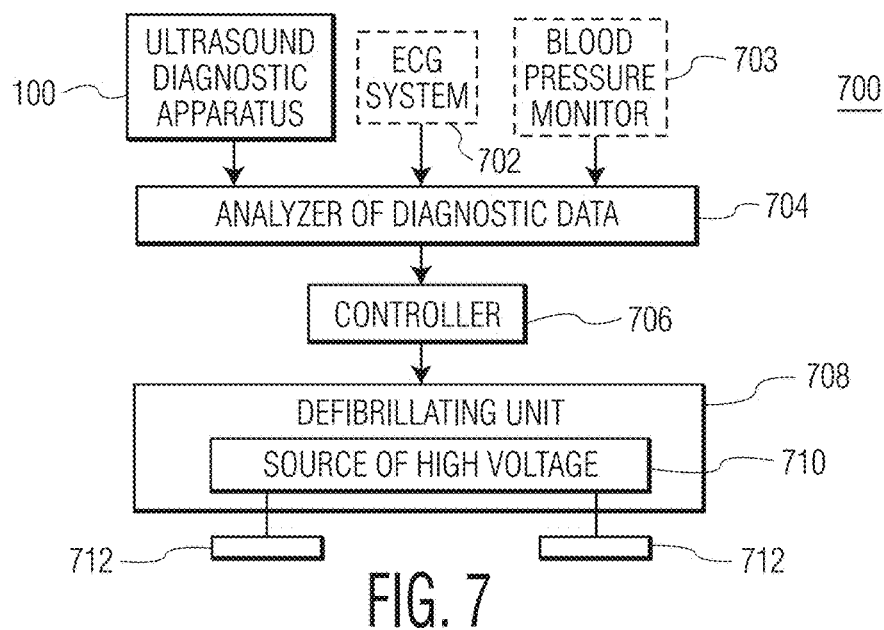
FIG. 7 depicts a block diagram of an exemplary defibrillating system including the ultrasound diagnostic apparatus of FIG. 5 in accordance with one embodiment of the present invention.

FIG. 7 depicts a block diagram of an exemplary programmable defibrillating system 700 in accordance with one embodiment of the present invention. Illustratively, the defibrillating system 700 comprises the ultrasound diagnostic apparatus 100 of FIG. 5, an optional ECG system 702, an optional blood pressure monitor 703, an analyzer 704 of diagnostic information, a defibrillating unit 708, and a programmable controller 706 of the defibrillating unit.

The apparatus 100 provides to the analyzer 704 diagnostic information relating to the mechanical activity of the heart and including at least one of the perfusion and the pulse state of a patient (e.g., the pulsation index PI). Ultrasonic diagnostic information may be obtained using the measurements performed on the patient's carotid artery. Such information may additionally be used in diagnosing, in real time, the state of blood supply to the brain of the patient.

In one embodiment, the ECG system 702 and the apparatus 100 acquire the diagnostic data simultaneously. In this embodiment, the signal related to the spectral distribution of the power of the Doppler signal may further be cross-correlated with an ECG signal. Such correlation may further increase accuracy and reliability of interpreting the diagnostic information by the analyzer 704.

In a further embodiment, each of the signals 142 may be coupled to the analyzer 704 where the signals 142 are selectively cross-correlated with the ECG signal to provide most accurate assessment of the perfusion, whereas the ABP monitor may be used as a source of data characterizing an overall state of mechanical activity of the heart. Alternatively, the analyzer 704 may use only the diagnostic information provided by the apparatus 100.

It should be noted, however, that the ECG signal corresponds to the electrical activity of the heart. Exclusive use of the ECG diagnostics in the system 700 may result in masking the lack of the mechanical activity (i.e., blood pumping functionality) of the patient's heart by the pulseless electrical activity (PEA) of the heart and, as such, cause erroneous clinical decisions.

The analyzer 704 performs analysis of collected information to determine whether to defibrillate the patient and define parameters of a defibrillation procedure. In operation, the analyzer 704 outputs the results of the analysis to the programmable controller 706 that configures the defibrillating unit 708 comprising a controlled source 710 of high voltage and application electrodes 712 (two electrodes 712 are shown) for executing the procedure.

In illustrative embodiments discussed in reference to FIGS. 5 and 7 above, many portions of apparatus 100 and system 700 are available in medical ultrasound and defibrillation systems and application specific integrated circuits (ASICs) available from Koninklijke Philips Electronics N.V. of Eindhoven, Netherlands.

What is claimed is:
1. A method of operating a defibrillation unit that utilizes an ultrasonic method for detecting and/or measuring pulsatile flow comprising:
  acquiring ultrasonic Doppler signal information from a flow site;
  determining from the Doppler signal information a power spectrum within a specific frequency band that comprises a banded Doppler signal;

identifying a fundamental and a plurality of harmonic peaks of the power spectrum of the banded Doppler signal within a plurality of discrete frequency ranges (i) that represent portions of the banded Doppler signal in which only periodic flow is present and (ii) that do not overlap;

determining a ratio of power of (i) the Doppler signal to (ii) baseline noise for each of the plurality of discrete frequency ranges that do not overlap and in which the fundamental and harmonic peaks of the power spectrum of the banded Doppler signal have been identified;

determining a measure of pulsatility of the pulsatile flow from a sum total of the power ratios of the Doppler signal to baseline noise determined for each of the plurality of discrete frequency ranges that do not overlap and in which the fundamental and harmonic peaks of the power spectrum of the banded Doppler signal have been identified; and controlling a defibrillation procedure, via a controller of the defibrillation unit, in response to the determined measure of pulsatility of the pulsatile flow.

2. The method of claim 1, wherein identifying further comprises identifying a fundamental and four harmonic peaks of the power spectrum.

3. The method of claim 1, wherein determining the power ratios further comprises calculating a normalized power ratio in each of the discrete frequency ranges including a respective fundamental or harmonic peak.

4. The method of claim 1, further comprising weighting the power ratio in each of the discrete frequency ranges as a function of noise.

5. The method of claim 4, wherein weighting the power ratio in each of the discrete frequency ranges further comprises weighting the power ratio in each of the discrete frequency ranges with a sigmoidal weighting function.

6. The method of claim 1, wherein determining a measure of pulsatility comprises combining the power ratio in each of the discrete frequency ranges to form a pulsation index.

7. The method of claim 6, further comprising comparing the pulsation index with a threshold.

8. The method of claim 1, further comprising determining a measure of noise from the power spectrum between the fundamental and harmonic peaks.

9. The method of claim 8, further comprising normalizing the measure of noise to total spectral power.

* * * * *